US005102408A

United States Patent [19]

Hamacher

[11] Patent Number: 5,102,408

[45] Date of Patent: Apr. 7, 1992

[54] FLUID MIXING RESERVOIR FOR USE IN MEDICAL PROCEDURES

[76] Inventor: Edward N. Hamacher, 707 W. 6th Ave., Apt. 13, Spokane, Wash. 99204

[21] Appl. No.: 514,588

[22] Filed: Apr. 26, 1990

[51] Int. Cl.[5] ............ A61B 19/00

[52] U.S. Cl. ............ 604/416; 604/410; 604/82; 604/87

[58] Field of Search ............ 604/410, 416, 403, 408, 604/409, 411, 415, 82, 86, 87

[56] References Cited

U.S. PATENT DOCUMENTS

| | | | |
|---|---|---|---|
| 3,554,256 | 1/1971 | Anderson | 150/8 |
| 4,131,200 | 12/1978 | Rinfret | 206/484 |
| 4,392,850 | 7/1983 | Elias et al. | 604/82 |
| 4,396,383 | 8/1983 | Hart | 604/416 X |
| 4,458,733 | 7/1984 | Lyons | 604/410 X |
| 4,467,588 | 8/1984 | Carveth | 53/425 |
| 4,484,920 | 11/1984 | Kaufman et al. | 604/410 X |
| 4,507,114 | 3/1985 | Bohman et al. | 604/416 X |
| 4,548,606 | 11/1985 | Larkin | 604/414 |
| 4,573,506 | 3/1986 | Paoletti | 141/98 |
| 4,576,603 | 3/1986 | Moss | 604/410 |
| 4,589,879 | 5/1986 | Pearson | 604/416 X |
| 4,610,684 | 9/1986 | Knox et al. | 604/416 |
| 4,645,073 | 2/1987 | Homan | 206/219 |
| 4,994,056 | 2/1991 | Ikeda | 604/410 |

FOREIGN PATENT DOCUMENTS

| | | | |
|---|---|---|---|
| 2346239 | 10/1977 | France | 604/416 |

*Primary Examiner*—Robert A. Hafer
*Assistant Examiner*—Kerry Owens
*Attorney, Agent, or Firm*—Michael J. Folise

[57] ABSTRACT

A sterile fluid mixing reservoir for storing premeasured quantities of fluids for subsequent combination is disclosed. The reservoir has a flexible outer bag which fully encloses one or more inner containers. The inner containers have self-opening mechanisms thereon which are manipulable through the outer bag. The bottles can be manufactured from a flexible material which facilitates intermixing of the fluids contained within the bag and inner containers.

8 Claims, 2 Drawing Sheets

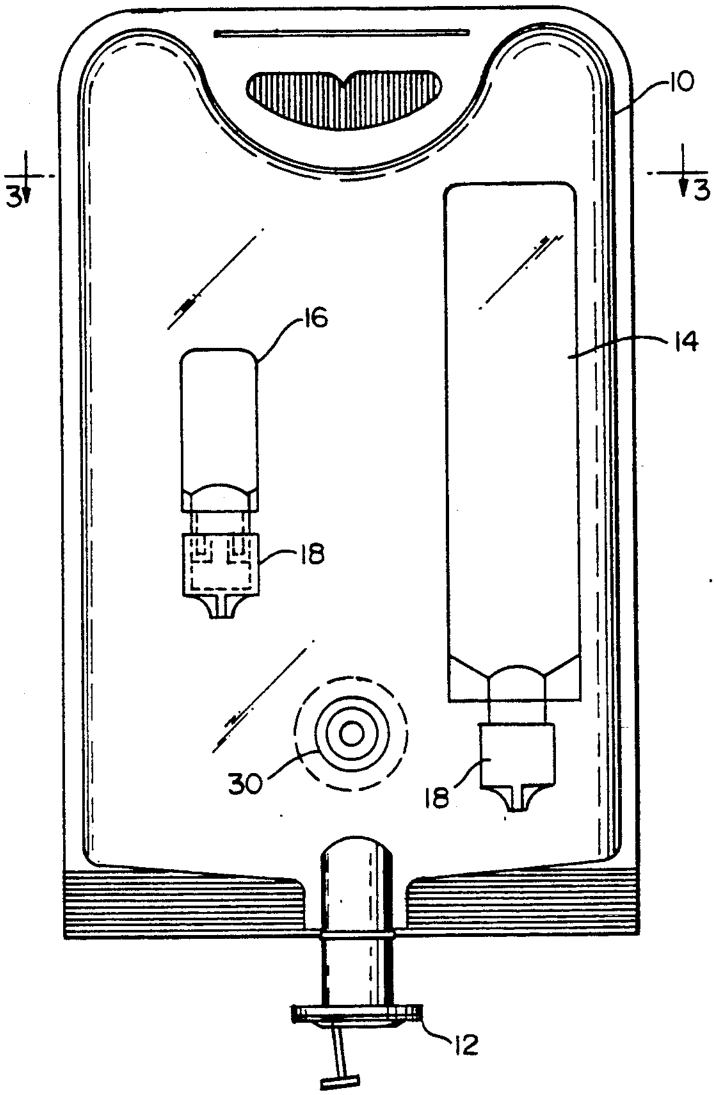
FIG. 1
FIG. 2
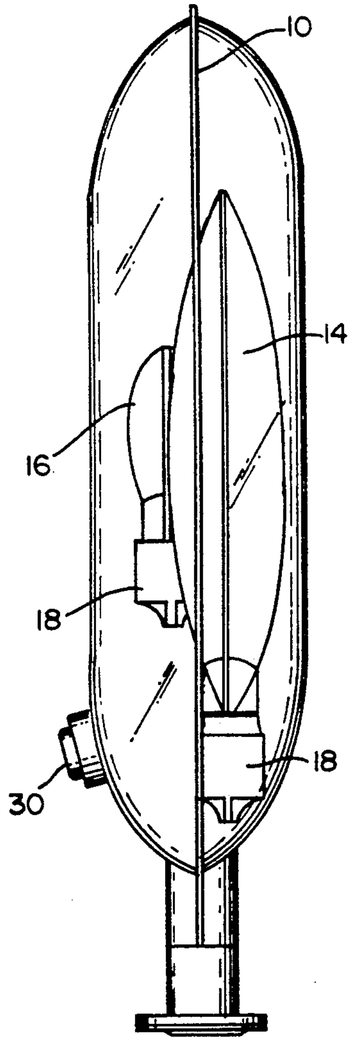
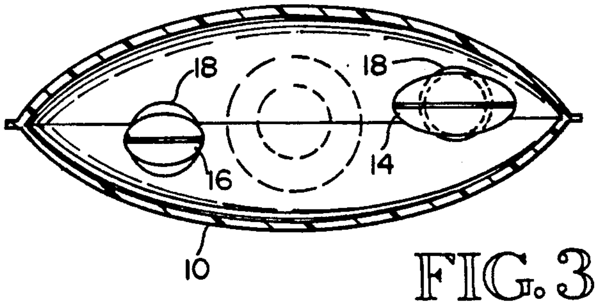
FIG. 3

FIG. 4
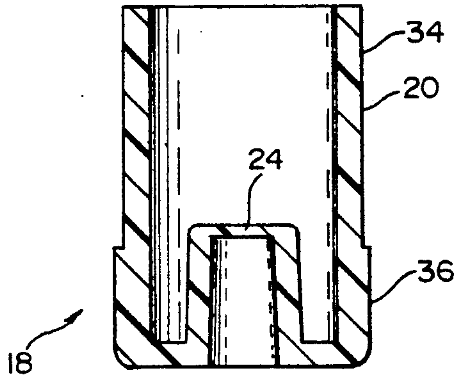
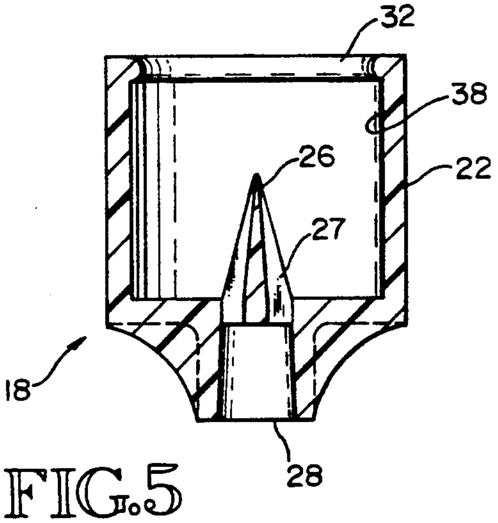
FIG. 5

FLUID MIXING RESERVOIR FOR USE IN MEDICAL PROCEDURES

DESCRIPTION

1. Technical Field

The invention is related to methods and apparatus for administering medicine. More specifically, the invention is related to devices for storing and mixing medicines.

2. Background of the Invention

One of the most significant risks for patients undergoing surgery is the use of a general anesthesia which places the patient in an unconscious state. Surgeons have therefore welcomed the introduction of local anesthetics and spinal anesthesia which allow some surgeries to be performed while the patient is conscious and, thus, without the risks associated with the use of general anesthesia. However, the variety of surgery which may be performed under conventional, local and spinal anesthesia is relatively limited.

I have developed a disassociative type of anesthesia which is as described in my U.S. Pat. No. 4,334,526, issued on June 15, 1982, entitled "METHOD FOR ADMINISTERING A DISASSOCIATIVE, CONSCIOUS TYPE OF ANESTHESIA," the disclosure of which is incorporated herein by reference which does not render the patient unconscious. This disassociation anesthesia is especially useful for aesthetic and reconstructive (plastic) surgery, intraoccular surgery and other surgeries that require a low dose 0.25% Xylocaine with 1:2,000,000 epinephrine which penetrates the subcutaneous layers, but which do not penetrate the muscle facia and abdominal cavities.

The advent of my disassociative type of anesthesia for aesthetic and reconstructive surgery has presented patients who would otherwise undergo surgery in a hospital setting under general anesthesia with the option of having such surgery in the hospital outpatient clinic or office operatory setting while in the conscious state. Thus, the risks and costs associated with this type of surgery have been dramatically reduced.

I have also developed infusion needles with Bullet Point tip(s) of various lengths and methods for using the same as is described in my U.S. Pat. Nos. 4,669,612 and 4,790,830, issued on Oct. 13, 1987 and Dec. 13, 1988, respectively, for delivering my low dose Xylocaine 0.25% with low dose epinephrine 1:2,000,000 anesthesia into into subcutaneous tissue over a large area through a single incision. The disclosures of these patents are also incorporated herein by reference.

I have further developed an infiltration pump described in my U.S. Pat. No. 4,612,010, issued on Sept. 16, 1986, for delivering large quantities of said low doses 0.25% Xylocaine with 1:2,000,000 epinephrine local anesthesia through said infusion needles. The disclosure of my U.S. Pat. No. 4,612,010 is also incorporated herein by reference. The disassociative anesthetic system, which comprises my infusion needles, infiltration pump and infiltration pump and low dose Xylocaine 0.25% with 1:2,000,000 epinephrine local anesthesia, has substantially reduced the hematomas associated with infiltration of local anesthetic with the sharp bevelled point needle, the complications associated with general anesthesia, and the cost of performing such surgeries in a hospital setting.

The anesthetic system described above relies on the use of a local anesthetic (Xylocaine) and a vasoconstrictor (epinephrine). Xylocaine is highly toxic if it is injected into the bloodstream. Therefore, great care must be taken to ensure that this medicine is not introduced directly into the bloodstream, and that the concentration of xylocaine delivered to the subcutaneous areas is maintained below a toxicity threshold. The vasoconstrictor epinephrine degrades when exposed to light, and therefore must be properly stored prior to mixing with the xylocaine.

Presently, plastic surgeons or nurses mix the medicines at the time of use in a bottle similar to an intravenous bottle or bag. A quantity of saline solution is also introduced into this mixture according to the specification set forth in my U.S. Pat. No. 4,334,526.

There are three potential problems associated with the preparation of the local xylocaine anesthesia described above:

(1) The medicines may be mixed in an improper ratio by the physician, anesthetist or nurse;

(2) The medicines may become contaminated if mixed in a non-sterile environment;

(3) The vasoconstrictor (epinephrine) may not be properly shielded when stored by the physician prior to mixture, and thus may have experienced photodegradation.

A number of devices for storing premeasured quantities of fluid for subsequent combination have been described. For example, U.S. Pat. No. 4,548,606 to Larkin describes a dual compartment or container for storing a medicament in a first compartment and a diluent in a second compartment. However, fluid communication between the two compartments is only established through a small passageway which would not promote sufficiently thorough mixing between the diluent and the medicament if the medicament was relatively toxic. U.S. Pat. No. 4,645,073 to Homan discloses an anticontamination hazardous material package which has an inner container and a flexible outer container. The inner container is fully enclosed by the outer container. However, the purpose of the outer container is merely to contain any leaks or spillage from the inner container. The volume between the inner and outer containers is not suitable for storing a fluid component (such as a buffer solution) for mixing with the component stored in the inner container. All of the other prior art devices known to the applicant suffer from similar limitations.

SUMMARY OF THE INVENTION

It is an object of the present invention to provide a technique for reducing the possibility of mixing the local Xylocaine anesthesia, vasoconstrictor and buffer solution in an improper ratio. It is a further object of the invention to prevent contamination of medicines during preparation of a mixture. It is yet another object of the invention to achieve the above two objects which reduce the possibility of photodegradation of at least one of the medicines.

The invention achieves these objects, and other objects and advantages which will become apparent from the description which follows, by providing a flexible outer bag which completely contains at least one selectively openable inner container for a medicine in which a mixing area is formed between the outer bag and inner container.

In the preferred embodiment of the invention, the outer bag is similar to a conventional intravenous bag with the appropriate ports and connectors for the introduction of a buffer solution into the bag and a connector for establishing fluid communication between the bag and a conventional intravenous tube. An opening mechanism is provided on the inner container which has a pierceable membrane. The opening mechanism can be operated through the outer flexible bag. The inner container may be flexible itself so that by squeezing the inner container through the outer bag the medicine in the inner container may be thoroughly mixed with a buffer solution in the outer bag. A second inner container may also be contained within the outer bag. One of the two inner containers can be manufactured from a substantially opaque material to prevent photodegradation of any medicament contained therein.

BRIEF DESCRIPTION OF THE DRAWINGS

FIG. 1 is a side elevational view of a fluid mixing reservoir in accordance with the present invention.

FIG. 2 is a side elevational view of the fluid mixing reservoir shown in FIG. 1.

FIG. 3 is a sectional view taken along line 3—3 of FIG. 1.

FIG. 4 is an enlarged, sectional, elevational view of a fixed part of a self-opening mechanism for use on an inner container.

FIG. 5 is an enlarged, sectional, elevational view of a moveable part of the self-opening mechanism which pierces a membrane on the fixed part shown on FIG. 4 to release fluid from an inner container.

DETAILED DESCRIPTION OF THE INVENTION

A fluid mixing reservoir for storing premeasured quantities of fluids for subsequent combination is shown in FIGS. 1-5. The invention ensures that medicines contained therein will be mixed in the proper ratios, are maintained in a sterile state and are fully protected from exposure to air, sunlight, or other agents which might otherwise degrade the efficacy of the medicines contained therein.

As shown in FIGS. 1-3, the invention includes a flexible plastic bag 10 sealed at one end with a connector 12 for a conventional intravenous tube (not shown). The bag is preferably manufactured from a clear polypropylene material.

A first plastic flask or bottle 14 is provided inside the bag for containing a first fluid such as a local anesthetic. A smaller, second plastic flask or bottle 16 is also fully enclosed within the bag 10. The second bottle or flask can be manufactured from an opaque plastic material to contain a light sensitive medicine such as a vasoconstrictor.

Each of the bottles 14, 16 are provided with a puncture or self-opening mechanism, generally indicated at reference numeral 18 in FIGS. 1-3 As best seen in FIGS. 4 and 5, the puncture mechanism 18 has a fixed part 20 which is connected to the bottles 14, 16 and a moveable part 22 which is received for reciprocal motion on the fixed part 20. The fixed part is sealed at one end by a thin diaphragm or membrane 24. The moveable part contains a spike 26 which will puncture the diaphragm 24 when the moveable part 22 is pressed towards the fixed part 20 of the bottles 14, 16. The spike portion has grooves or flutes 27 which form a fluid passageway through the spike. An aperture 28 in the moveable part 22, the flutes in the spike and the punctured portion of the membrane 24 form a complete escape route for fluid in the inner containers.

The fixed and moveable parts 20, 22 are generally annular in shape, and are preferably manufactured from an injection molded thermoplastic material. The moveable part 22 has an inner, circumferential lip 32 having an inner diameter slightly larger than the external diameter 34 of the fixed part 20. The fixed part has an enlarged section 36 having a diameter slightly larger than the inner diameter of the lip 32 and slightly smaller than the diameter of an inner wall 38 of the moveable part 22.

When the fixed and moveable parts 20, 22 are engaged as shown in FIGS. 1-3, the lip 32 guides the moveable part 22 for reciprocal motion over the outer surface 34 of the fixed part 20. The enlarged section 36 on the fixed part 20 prevents the moveable part from becoming disengaged from the bottles 14, 16.

EXAMPLES

EXAMPLE 1

The fluid mixing reservoir of the present invention is used for storing, mixing and delivering a solution of Xylocaine 0.25% with 1:2,000,000 epinephrine local anesthetic. The first plastic bottle 14 has a volume of approximately 40 ml, and is filled with 31.25 ml of a 4% solution of a local anesthetic, xylocaine.

The second plastic bottle 16 has a volume of approximately 1 ml and is filled with 0.25 ml of a solution of a vasoconstrictor, epinephrine. The flexible plastic bag 10 preferably has a volume of 550 ml and is filled with 468.5 ml of 0.9% normal saline. Total solution of 0.25% Xylocaine with 1:2,000,000 epinephrine is 500 ml. Total bag capacity is 550 ml.

To mix the solutions, the movable parts 22 of each of the bottles 14, 16 are then operated through the flexible plastic bag such that the membranes 24 are punctured to release the contents therefrom. The bottles 14, 16 are squeezed to facilitate the release of their fluid contents.

In an alternate embodiment, the flexible plastic bag is not pre-loaded with saline solution and the physician, anesthetist, or nurse introduces a saline buffer solution into the outer, flexible plastic bag 10 through a port 30. A volume of 468.5 ml of buffer solution is preferably introduced into the bag through a self-sealing membrane on the port 30. The moveable parts 22 of each of bottles 14, 16 are then operated through the flexible plastic bag such that the membranes 24 are punctured to release the contents therefrom. The bottles 14, 16 are squeezed to facilitate the release of their fluid contents. After the anesthetic, vasoconstrictor and buffer solutions are thoroughly mixed, a conventional intravenous drip tube is connected to the connector 12 to connect the fluid mixing reservoir to other portions of the anesthetic delivery system. The remaining portions of the anesthetic delivery system may comprise my infusion pump and infiltration needles for infiltration of subcutaneous tissues prior to all fields of surgical specialties or drug medications by IV drip.

Other embodiments and variations of the invention are also contemplated. The invention could be used with only one internal container, although for the example described above two are preferred. Furthermore, more than two internal containers may be used for different surgical procedures. Self-opening mechanisms of differing construction could be used. Therefore, the invention is not to be limited by the above description, but is to be determined in scope by the claims which follow.

I claim:

1. A sterile fluid mixing reservoir for storing premeasured quantities of fluids for subsequent combination, comprising:

a sealed, outer, flexible container defining a volume;

at least two free floating, flexible inner containers within the volume, completely enclosed by the outer container for storing premeasured quantities of fluids; and one self-opening mechanism only on each of the inner containers for initially sealing the inner containers, the self-opening mechanisms each having a fixed portion connected to the inner container and a moveable portion which is manipulable through the flexible outer container for selectively releasing the fluid contained therein.

2. The fluid mixing reservoir of claim 1 wherein at least one of the inner containers is substantially opaque to minimize photodegradation of the fluid stored therein.

3. The fluid mixing reservoir of claim 1 wherein the fixed portion of the self-opening member has a relatively thin membrane thereon and wherein the moveable portion has a piercing member located thereon so that when the moveable portion is manipulated, the membrane fixed portion is pierced and the fluid in the inner container is released.

4. The fluid mixing reservoir of claim 1 wherein the outer container has a self-sealing port thereon so that a solution can be introduced into the outer container with a hypodermic syringe.

5. A sterile fluid mixing reservoir for storing premeasured quantities of fluids for subsequent combination, comprising:

a sealed, outer, flexible container defining a volume;

an inner free floating container within the volume, completely enclosed by the outer container for storing a premeasured quantity of fluid; and a self-opening mechanism on the inner container for initially sealing the inner container, the self-opening mechanism having a fixed portion connected to the inner container and a moveable portion which is manipulable through the flexible outer container for selectively releasing the fluid contained therein for mixing with any fluid contents of the outer container.

6. The fluid mixing reservoir of claim 5 wherein the inner container is substantially opaque to minimize photodegradation of the fluid stored therein.

7. The fluid mixing reservoir of claim 5 wherein the fixed portion of the self-opening member has a relatively thin membrane thereon and wherein the moveable portion has a piercing member located thereon so that when the moveable portion is manipulated, the membrane fixed portion is pierced and the fluid in the inner container is released.

8. The fluid mixing reservoir of claim 5 wherein the outer container has a self-sealing port thereon so that a solution can be introduced into the outer container with a hypodermic syringe.

* * * * *